US00PP26308P3

(12) United States Plant Patent
Barrault

(10) Patent No.: US PP26,308 P3
(45) Date of Patent: Jan. 12, 2016

(54) ***SALVIA* PLANT NAMED 'BARSAL'**

(50) Latin Name: ***Salvia* hybrid**
Varietal Denomination: BARSAL

(71) Applicant: Michel Barrault, La Possonniere (FR)

(72) Inventor: Michel Barrault, La Possonniere (FR)

( * ) Notice: Subject to any disclaimer, the term of this patent is extended or adjusted under 35 U.S.C. 154(b) by 118 days.

(21) Appl. No.: 13/987,632

(22) Filed: Aug. 16, 2013

(65) Prior Publication Data

US 2015/0052653 P1 Feb. 19, 2015

(51) Int. Cl.
*A01H 5/02* (2006.01)

(52) U.S. Cl.
USPC ..... Plt./475
CPC ..... *A01H 5/02* (2013.01)

(58) Field of Classification Search
USPC ..... Plt./475
See application file for complete search history.

(56) References Cited

PUBLICATIONS

New Plants and Flowers, Jan. 21, 2013.*

* cited by examiner

*Primary Examiner* — Keith O. Robinson
(74) *Attorney, Agent, or Firm* — Cassandra Bright

(57) ABSTRACT

A new and distinct *Salvia* cultivar named 'BARSAL' is disclosed, characterized by an attractive upright plant habit, easily producing lateral branches. 'BARSAL' produces violet flowers continuously from May to November. The new variety is a *Salvia*, normally produced as an outdoor garden or container plant.

2 Drawing Sheets

Latin name of the genus and species: *Salvia* hybrid.
Variety denomination: 'BARSAL'.

BACKGROUND OF THE INVENTION

The new cultivar is a product of chance discovery by the inventor, Michel Barrault, a citizen of France. The new variety was discovered as an individual seedling during 2010 t a commercial nursery in Maine de Loire, France. The parent varieties are unknown, however the inventor's best information leads him to believe the seed parent is the commercial, unpatented variety Salvia gregii 'Lycoides'. The pollen parent is unknown.

Asexual reproduction of the new cultivar 'BARSAL' by vegetative cuttings was first performed at the same commercial greenhouse in La Possoniere, France in 2010 and has shown that the unique features of this cultivar are stable and reproduced true to type on successive generations.

SUMMARY OF THE INVENTION

The cultivar 'BARSAL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BARSAL'. These characteristics in combination distinguish 'BARSAL' as a new and distinct *Salvia* cultivar:

1. Violet colored flowers.
2. Well shaped, upright plant habit.
3. Continuous flowering from May to November.
4. Easy branching.
5. Larger flower size.

COMMERCIAL COMPARISONS

Plants of the new cultivar 'BARSAL' can be compared to the unpatented variety *Salvia gregii* 'Lycoides'. Plants of 'BARSAL' are similar to plants of, *Salvia gregii* 'Lycoides' in most horticultural characteristics, however, plants of the new cultivar 'BARSAL' are overall taller, and produce lateral branches more easily. 'BARSAL' also produces flowers that are more true violet, less violet-blue colored than *Salvia greggii* 'Lycoides'.

Plants of the new cultivar 'BARSAL' can also be compared to the unpatented variety *Salvia gregii* 'Diane'. Plants of 'BARSAL' are similar to plants of, *Salvia* 'Diane' in most horticultural characteristics, however, plants of the new cultivar 'BARSAL' are taller and more vigorous, and flower all Summer. 'BARSAL' also produces darker purple flowers than 'Diane'.

Plants of the new cultivar 'BARSAL' can also be compared to the unpatented variety *Salvia* hybrid 'Nuit d'Armor'. Plants of 'BARSAL' are similar to plants of, *Salvia* hybrid 'Nuit d'Armor' in most horticultural characteristics, however, plants of the new cultivar 'BARSAL' are taller, more upright, and less spreading than plants of Nuit d'Armor. Additionally, flower color of 'BARSAL' is violet, compared to the blue flowers of 'Nuit d'Armor'.

BRIEF DESCRIPTION OF THE PHOTOGRAPHS

Figure 1:
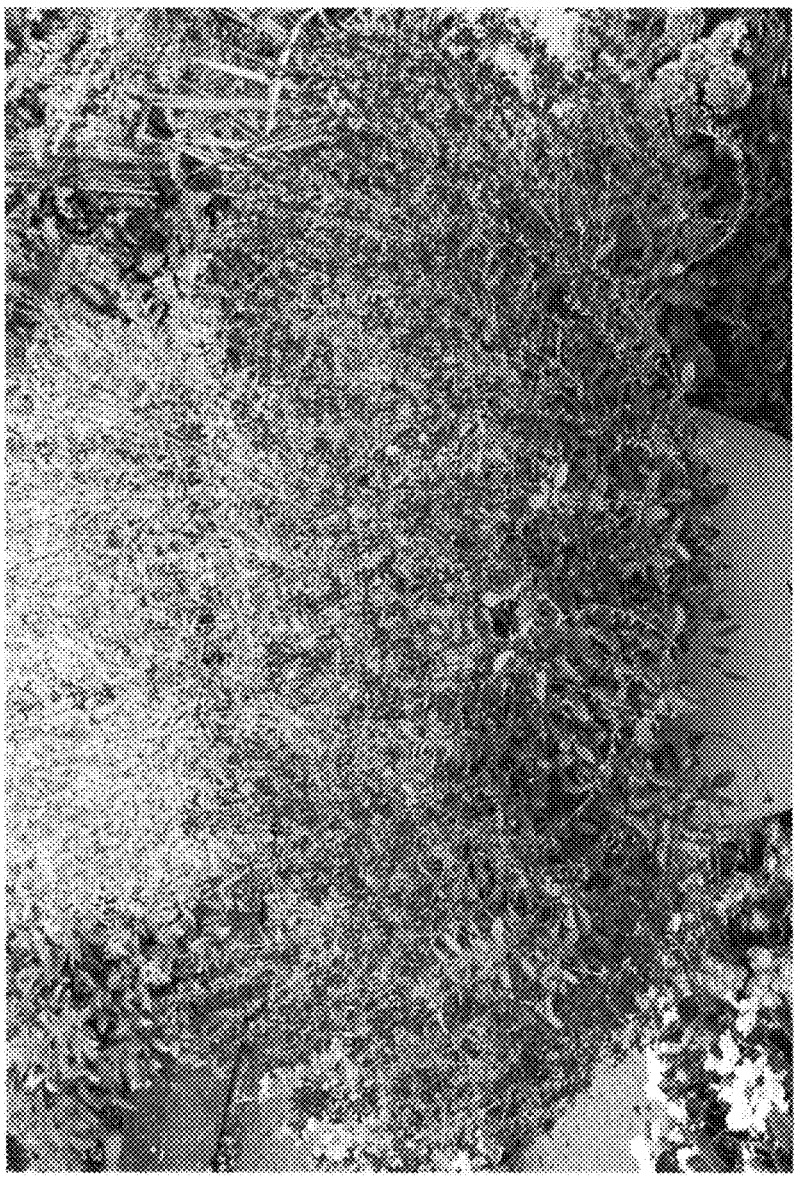

The accompanying photograph in FIG. 1 illustrates in full color a flowering plant of 'BARSAL'. Age of the plant is approximately 18 months.

Figure 2:
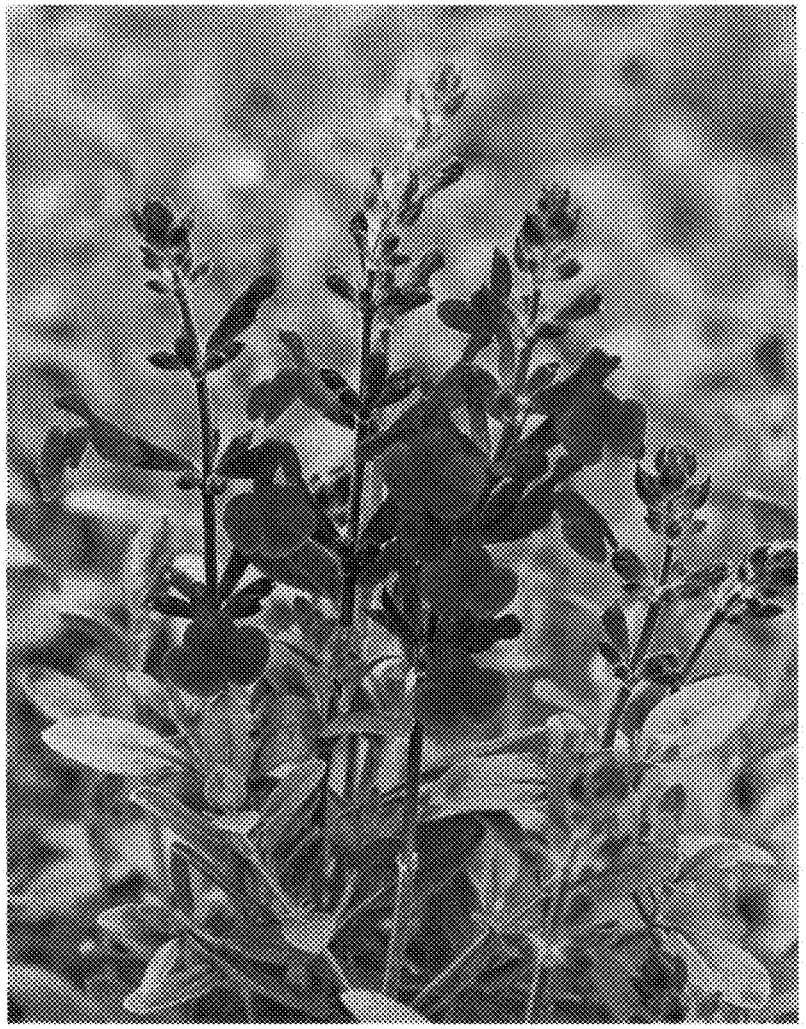

FIG. 2 illustrates in full color typical flowering spike of 'BARSAL' grown outdoors, in a garden.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BARSAL' plants grown outdoors at a commercial nursery in Possonniere, France. The growing temperature ranged from 8° C. to 28° C., day and night. The nursery area is un-shaded, giving bright, normal sunlight conditions. Measurements and numerical values represent averages of typical plant types.
Botanical classification: *Salvia* hybrid 'BARSAL'.

PROPAGATION

Time to initiate roots: About 10 days at approximately 20° C.
Time to produce a rooted cutting: About 20 to 25 days at 20° C.
Root description: Fibrous, well branched. Colored near RHS Grey-Brown N199A.

PLANT

Plant height: Approximately 60 cm.
Plant spread: Approximately 80 cm.
Growth rate: Moderate.
Branching characteristics: Plants branch easily from a pinch. Upper portion of plant branches easily on its own, making new branches approximately every 5 to 15 cm.
Length of primary lateral branches: Approximately 30 to 35 cm.
Diameter of lateral branches: Approximately 0.20 to 0.30 cm.
Quantity of lateral branches: About 50 to 60.
Stem:
- *Color*.—Young: Near RHS Green-Yellow 145A and oldest: Near RHS Greyed-Orange 165A.
- *Texture/pubescence*.—Non pubescent, very slightly scaly.

Internode length: Approximately 3.0 to 4.5 cm.
Age of plant described: Approximately 30 weeks in a 2 liter container.

FOLIAGE

Leaf:
- *Arrangement*.—Opposite.
- *Type*.—Single.
- *Quantity*.—Approximately 12 to 16 per main branch.
- *Average length*.—Approximately 3.0 to 5.8 cm.
- *Average width*.—Approximately 1.0 to 1.5 cm.
- *Shape of blade*.—Elliptic.
- *Apex*.—Acute.
- *Base*.—Attenuate.
- *Attachment*.—Stalked.
- *Margin*.—Shallow crenate.
- *Texture of top surface*.—Non pubescent.
- *Texture of bottom surface*.—Non pubescent.
- *Color*.—Young foliage upper side: Near RHS Yellow green 138A. Young foliage under side: Near RHS Yellow green 138A. Mature foliage upper side: Near RHS green 137A. Mature foliage under side: Near RHS green 138A.
- *Venation*.—Type: Pinnate. Venation color upper side: Near RHS yellow green 145A. Venation color under side: Near RHS Yellow-Green 144B upper side. Under side near Yellow-Green 144C.
- *Petiole*.—Average Length: Approximately 1.0 to 1.4 cm. Diameter: Approximately 0.1 cm. Color: Near RHS Yellow-Green 144B. Texture: Glabrous. Strength: Flexible.

FLOWER

Natural flowering season: May to November in France.
Inflorescence type and habit: Bilabiate flowers arranged in verticillasters on spikes. Corolla self-cleaning, calyx persists.
Flower longevity on plant: Approximately 9 days.
Fragrance: Faint to none.
Quantity of flowers: About 12 to 16 buds and 8 to 10 fully opened flowers per lateral branch, at one time; or about 50 to 60 blooming spikes per plant, on a 1 year old plant. Mature plants, more than 2 years old can have 200 blooming spikes.
Inflorescence size:
- *Diameter/width*.—Approximately 4 to 6 cm.
- *Height*.—Approximately 12 to 16 cm.

Peduncle:
- *Length*.—Average 5.0 cm.
- *Diameter*.—0.3 cm.
- *Color*.—Near RHS Yellow-Green 144A.
- *Orientation*.—Nearly completely vertical (10 degrees angle).
- *Strength*.—Rigid.
- *Texture*.—Lightly pubescent ridged.

Pedicel:
- *Length*.—Average 0.50 cm.
- *Diameter*.—0.10 cm.
- *Color*.—Near RHS Greyed-Purple N187A.
- *Orientation*.—Approximately 35 degrees from peduncle.
- *Strength*.—Rigid.
- *Texture*.—Lightly pubescent ridged.

Individual flowers:
- *Length*.—Average 2.9 cm.
- *Diameter*.—1.5 cm.

Petals:
- *Petal arrangement*.—Fused: flower-cup with 2 lips.
- *Margin*.—Entire.
- *Length*.—Lower lip: 1.1 to 1.2 cm upper lip: 1.8 to 2.0 cm.
- *Width*.—Lower lip: 1.1 to 1.4 cm upper lip: 0.2 to 0.4 cm.
- *Petal quantity*.—2 lips.
- *Petal apex shape*.—Lobate for lower lip.
- *Texture*.—Smooth to somewhat velvety.
- *Color*.—Petals: When opening: Upper surface: Near RHS Violet N88A. Lower surface: Near RHS Violet N88A. Fully opened: Upper surface: Near RHS Violet N88A. Lower surface: Near RHS Violet N88A. Fading: Upper surface: Near RHS Violet 86A. Lower surface: Near RHS Violet 86A.

Bud:
- *Shape*.—Elongated cylinder.
- *Length*.—0.8 to 1.0 cm.
- *Diameter*.—0.2 to 0.3 cm.
- *Color*.—Near RHS Violet 83A.
- *Texture*.—Pubescent.

Sepals:

*Shape*.—Fused cylinder.

*Quantity per flower*.—3.

*Length*.—Approximately 1.0 to 1.2 cm.

*Width*.—Approximately largest 0.3 cm and 2 smaller: 0.2 cm.

*Apex*.—Acute.

*Base*.—Fused.

*Margin*.—Entire.

*Texture*.—Pubescent.

*Color*.—Inner and outer surfaces: Background color near RHS Green 138A, covered in a heavy flush of Violet 83A.

REPRODUCTIVE ORGANS

Stamens:

*Number*.—2.

*Filament length*.—Approximately 0.8 to 0.9 cm.

Anthers:

*Shape*.—Linear.

*Length*.—Approximately 0.15 cm.

*Diameter*.—Less than 1 mm.

*Color*.—Near RHS Violet 83B.

*Pollen*.—Color: Near RHS Yellow orange 17B. Quantity: Moderate.

Pistil:

*Number*.—1.

*Length*.—Approximately 1.2 to 1.4 cm.

*Style*.—Length: Approximately 1.0 to 1.2 cm. Color: Near RHS Violet 84D.

*Stigma*.—Shape: Linear. Color: Near RHS Violet 86A. Ovary color: Near RHS Yellow-Green 150B.

OTHER CHARACTERISTICS

Seeds and fruits: Infrequent seed production. When seeds do occur, approximately 4 seeds per flower, spherical shape. Approximately 1 mm in diameter. Dark Grey-Brown in color, not accurately measured with RHS chart due to size.

Disease/pest resistance: Neither resistance nor susceptibility to pathogens and pests common to *Salvia* have been observed. Variety exhibits normal resistance to diseases and no exceptional susceptibility or tolerance to pests.

Temperature tolerance: The new variety tolerates temperatures approximately between 5 to 35° C.

What is claimed is:

1. A new and distinct cultivar of *Salvia* plant named 'BARSAL' as herein illustrated and described.

* * * * *